US006432639B1

(12) United States Patent
Lichter et al.

(10) Patent No.: US 6,432,639 B1
(45) Date of Patent: Aug. 13, 2002

(54) ISOLATED CYP3A4 NUCLEIC ACID MOLECULES AND DETECTION METHODS

(75) Inventors: Jay B. Lichter; Marco Guida, both of San Diego, CA (US)

(73) Assignee: DNA Sciences Laboratories, Inc., Morrisville, NC (US)

( * ) Notice: Subject to any disclaimer, the term of this patent is extended or adjusted under 35 U.S.C. 154(b) by 0 days.

(21) Appl. No.: 09/144,367

(22) Filed: Aug. 31, 1998

Related U.S. Application Data

(60) Provisional application No. 60/058,612, filed on Sep. 10, 1997.

(51) Int. Cl.[7] .......................... C12Q 1/68; C07H 21/04
(52) U.S. Cl. ......................... 435/6; 536/23.2; 536/23.5; 536/24.31
(58) Field of Search .................. 435/6, 91.2; 536/23.2, 536/23.5, 24.31

(56) References Cited

U.S. PATENT DOCUMENTS

| | | | |
|---|---|---|---|
| 5,413,915 A | 5/1995 | Case et al. ..................... 435/25 |
| 5,420,027 A | 5/1995 | Fisher et al. ................. 435/189 |
| 5,445,934 A | 8/1995 | Fodor et al. ..................... 435/6 |
| 5,478,723 A | 12/1995 | Parkinson et al. ............. 435/4 |
| 5,506,131 A | 4/1996 | Harris et al. ............. 435/240.2 |
| 5,660,986 A | 8/1997 | Harris et al. ................... 435/6 |
| 6,174,684 B1 | 1/2001 | Rebbeck et al. ................ 435/6 |
| 6,183,963 B1 * | 2/2001 | Sinnett .......................... 435/6 |

FOREIGN PATENT DOCUMENTS

| | | | |
|---|---|---|---|
| WO | 92/19647 | * 11/1992 |
| WO | 93/18178 | * 9/1993 |
| WO | 95/35505 | 12/1995 |

OTHER PUBLICATIONS

Peyronneau, J. et al. Eur. J. Biochem. 218:355–361, Dec. 1993.*
Hllbert, T.P. et al. J. Biol. Chem. 272(10):6733–40, Mar. 1997.*
Skolnick, A.A. J. Am. Med. Assn. 275(8):581–2, Feb. 1996.*
Westlind, A. et al. Biochem. Biophys. Res. Comm. 259:201–205, May 1999.*
Waye, M.M.Y. et al. GenBank Accession No. R41114, May 1995.*
Waye, M.M.Y. et al. Protein Engineering 8(Suppl):90 (Miami Winter BioTechnology Symp. Proc.), 1995.*
Wilson, R. et al. GenBank Accession No. U46669, Jan. 1996.*
Wilson, R. et al. Nature 368:32–38, Mar. 1994.*
Hillier, L. et al. GenBank Accession No. H21215, Jul. 1995.*
Sulston, J. GenBank Accession No. Z73358, Jul. 1996.*
Kawagishi, M. GenBank Accession No. X59297, Dec. 1991.*
Marra, M. et al. GenBank Accession No. W35854, Sep. 1996.*
Carter, P.E. et al. Eur. J. Biochem. 197(2):301–308, May 1995.*
Brian, William R., et al., "Catalytic Activities Of Human Liver Cytochrome P–450 IIIA4 Expressed In *Saccharomyces Cerevisiae,*" *Biochemistry* (1990) vol. 29:11280–11292.
Delahunty, Claire, et al., "Testing The Feasibility Of DNA Typing For Human Identification By PCR And An Oligonucleotide Ligation Assay," *Am. J. Hum. Genet.* (1996) vol. 581239–1246.
DeRisi, Joseph, et al., "Use Of A cDNA Microarray To Analyze Gene Expression Patterns In Human Cancer," *Nature Genetics* (Dec. 1996) vol. 14:457–460.
Genbank Accession No. D11131, Hashimoto, H. et al, Jan. 1994.
Genbank Accession No. M18907, Gonzalez, F.J. et al, Jun. 1989.
Genbank Accession No. S74700, Jounaidi, Y. et al, Apr. 1995.
Golovleve, Irina, et al., "Polymorphism In The Interferon–α Gene Family," *Am. J. Hum. Genet.* (1996) vol. 59:570–578.
Hacia, Jospeh G., et al., "Detection Of Heterozygous Mutations In BRCA1 Using High Density Oligonucleotide Arrays And Two–Colour Fluorescence Analysis," *Nature Genetics* (Dec. 1996) vol. 14:441–447.
Hashimoto, Hisashi, et al., "Gene Structures Of *CYP3A4*, An Adult–Specific Form Of Cytochrome P450 In Human Livers, And Its Transcriptional control," *Eur. J. Biochem.* (1993) vol. 218:585–595.
Lewis, David F.V., et al., "Molecular Modeling And Quantitative Structure–Activity Relationship Studies On The Interaction Of Omeprazole With Cytochrome P450 Isozymes," *Toxicology* (1998) vol. 125:31–44.
Lockhart, David J., et al., "Expression Monitoring By Hybridization To High–Density Oligonucleotide Arrays," *Nature Biotechnology* (Dec. 1996) vol. 14:1675–1680.
Lown, Kenneth S., et al., "Grapefruit Juice Increases Felodipine Oral Availabiltiy In Humans By Decreasing Intestinal CYP3A Protein Expression," *J. Clin. Invest. The American Society For Clinical Investigation, Inc.* (May 1997) vol. 99, No. (10):2545–2553.

(List continued on next page.)

*Primary Examiner*—W. Gary Jones
*Assistant Examiner*—Diana Johannsen
(74) *Attorney, Agent, or Firm*—Sheridan Ross P.C.

(57) ABSTRACT

Genetic polymorphisms are identified in the human CYP3A4 gene that alter CYP3A4-dependent drug metabolism. Nucleic acids comprising the polymorphic sequences are used to screen patients for altered metabolism for CYP3A4 substrates, potential drug-drug interactions, and adverse/side effects, as well as diseases that result from environmental or occupational exposure to toxins. The nucleic acids are used to establish animal, cell and in vitro models for drug metabolism.

15 Claims, No Drawings

OTHER PUBLICATIONS

Mansfield, David C., et al., "Automation Of Genetic Linkage Analysis Using Fluorescent Microsatellite Markers," *Genomics* (1994) vol. 24:225–233.

Sachse, Christoph, et al., "Cytochrome P450 2D6 Variants In A Caucasian Population: Allele Frequencies And Phenotypic Consequences," *Am. J. Hum. Genet.* (1997) vol. 60:284–295.

Saiki, Randall K., et al., "Primer–Directed Enzymatic Amplification Of DNA With A Thermostable DNA Polymerase," *Science* (Jan. 29, 1988) vol. 239:441–532.

Sambrook, J., et al., "In Vitro Amplification Of DNA By The Polymerase Chain Reaction," *Molecular Cloning, A Laboratory Manual, Second Edition, Cold Spring Harbor Laboratory Press* (1989) pp:14.2–14.35.

Schuetz, Erin G., et al., "Modulators And Substrates Of P–Glycoprotein And Cytochrome P4503A Coordinately Up–Regulate These Proteins In Human Colon Carcinoma Cells," *Molecular Pharmacology* (1996) vol. 49:311–318.

Underhill, Peter A., et al., "A Pre–Columbian Y Chromosome–Specific Transition And Its Implications For Human Evolutionary History," *Proc. Natl. Acad. Sci. USA* (Jan. 1996) vol. 93:196–200.

Yamazaki, Hiroshi, et al., "Reconstitution Of Recombinant Cytochrome P450 2C10(2C9) And Comparison With Cytochrome P450 3A4 And Other Forms: Effects Of Cytochrome P450–P450 And Cytochrome P450–$b_5$ Interactions[1]," *Archives Of Biochemistry And Biophysics* (1997) vol. 342, No. (2):329–337.

Ziegle, Janet S., et al., "Application Of Automated DNA Sizing Technology For Genotyping Microsatellite Loci," *Genomics* (1992) vol. 14:1026–1031.

* cited by examiner

SEQUENCE LISTING

<160> NUMBER OF SEQ ID NOS: 58

<210> SEQ ID NO 1
<211> LENGTH: 2759
<212> TYPE: DNA
<213> ORGANISM: H. sapiens
<220> FEATURE:
<221> NAME/KEY: CDS
<222> LOCATION: (70)...(1581)
<223> OTHER INFORMATION: Human CYP3A4 cDNA reference sequence

<400> SEQUENCE: 1

```
gaattcccaa agagcaacac agagctgaaa ggaagactca gaggagagag ataagtaagg      60 aaagtagtg atg gct ctc atc cca gac ttg gcc atg gaa acc tgg ctt ctc     111
         Met Ala Leu Ile Pro Asp Leu Ala Met Glu Thr Trp Leu Leu
          1               5                  10 ctg gct gtc agc ctg gtg ctc ctc tat cta tat gga acc cat tca cat     159
Leu Ala Val Ser Leu Val Leu Leu Tyr Leu Tyr Gly Thr His Ser His
 15                  20                  25                  30 gga ctt ttt aag aag ctt gga att cca ggg ccc aca cct ctg cct ttt     207
Gly Leu Phe Lys Lys Leu Gly Ile Pro Gly Pro Thr Pro Leu Pro Phe
                 35                  40                  45 ttg gga aat att ttg tcc tac cat aag ggc ttt tgt atg ttt gac atg     255
Leu Gly Asn Ile Leu Ser Tyr His Lys Gly Phe Cys Met Phe Asp Met
             50                  55                  60 gaa tgt cat aaa aag tat gga aaa gtg tgg ggc ttt tat gat ggt caa     303
Glu Cys His Lys Lys Tyr Gly Lys Val Trp Gly Phe Tyr Asp Gly Gln
         65                  70                  75 cag cct gtg ctg gct atc aca gat cct gac atg atc aaa aca gtg cta     351
Gln Pro Val Leu Ala Ile Thr Asp Pro Asp Met Ile Lys Thr Val Leu
     80                  85                  90 gtg aaa gaa tgt tat tct gtc ttc aca aac cgg agg cct ttt ggt cca     399
Val Lys Glu Cys Tyr Ser Val Phe Thr Asn Arg Arg Pro Phe Gly Pro
 95                 100                 105                 110
```

```
gtg gga ttt atg aaa agt gcc atc tct ata gct gag gat gaa gaa tgg    447
Val Gly Phe Met Lys Ser Ala Ile Ser Ile Ala Glu Asp Glu Glu Trp
            115                 120                 125 aag aga tta cga tca ttg ctg tct cca acc ttc acc agt gga aaa ctc    495
Lys Arg Leu Arg Ser Leu Leu Ser Pro Thr Phe Thr Ser Gly Lys Leu
        130                 135                 140 aag gag atg gtc cct atc att gcc cag tat gga gat gtg ttg gtg aga    543
Lys Glu Met Val Pro Ile Ile Ala Gln Tyr Gly Asp Val Leu Val Arg
    145                 150                 155 aat ctg agg cgg gaa gca gag aca ggc aag cct gtc acc ttg aaa gac    591
Asn Leu Arg Arg Glu Ala Glu Thr Gly Lys Pro Val Thr Leu Lys Asp
160                 165                 170 gtc ttt ggg gcc tac agc atg gat gtg atc act agc aca tca ttt gga    639
Val Phe Gly Ala Tyr Ser Met Asp Val Ile Thr Ser Thr Ser Phe Gly
175                 180                 185                 190 gtg aac atc gac tct ctc aac aat cca caa gac ccc ttt gtg gaa aac    687
Val Asn Ile Asp Ser Leu Asn Asn Pro Gln Asp Pro Phe Val Glu Asn
            195                 200                 205 acc aag aag ctt tta aga ttt gat ttt ttg gat cca ttc ttt ctc tca    735
Thr Lys Lys Leu Leu Arg Phe Asp Phe Leu Asp Pro Phe Phe Leu Ser
        210                 215                 220 ata aca gtc ttt cca ttc ctc atc cca att ctt gaa gta tta aat atc    783
Ile Thr Val Phe Pro Phe Leu Ile Pro Ile Leu Glu Val Leu Asn Ile
    225                 230                 235 tgt gtg ttt cca aga gaa gtt aca aat ttt tta aga aaa tct gta aaa    831
Cys Val Phe Pro Arg Glu Val Thr Asn Phe Leu Arg Lys Ser Val Lys
240                 245                 250 agg atg aaa gaa agt cgc ctc gaa gat aca caa aag cac cga gtg gat    879
Arg Met Lys Glu Ser Arg Leu Glu Asp Thr Gln Lys His Arg Val Asp
255                 260                 265                 270 ttc ctt cag ctg atg att gac tct cag aat tca aaa gaa act gag tcc    927
Phe Leu Gln Leu Met Ile Asp Ser Gln Asn Ser Lys Glu Thr Glu Ser
            275                 280                 285 cac aaa gct ctg tcc gat ctg gag ctc gtg gcc caa tca att atc ttt    975
His Lys Ala Leu Ser Asp Leu Glu Leu Val Ala Gln Ser Ile Ile Phe
        290                 295                 300 att ttt gct ggc tat gaa acc acg agc agt gtt ctc tcc ttc att atg    1023
Ile Phe Ala Gly Tyr Glu Thr Thr Ser Ser Val Leu Ser Phe Ile Met
    305                 310                 315 tat gaa ctg gcc act cac cct gat gtc cag cag aaa ctg cag gag gaa    1071
Tyr Glu Leu Ala Thr His Pro Asp Val Gln Gln Lys Leu Gln Glu Glu
320                 325                 330 att gat gca gtt tta ccc aat aag gca cca ccc acc tat gat act gtg    1119
Ile Asp Ala Val Leu Pro Asn Lys Ala Pro Pro Thr Tyr Asp Thr Val
335                 340                 345                 350 cta cag atg gag tat ctt gac atg gtg gtg aat gaa acg ctc aga tta    1167
Leu Gln Met Glu Tyr Leu Asp Met Val Val Asn Glu Thr Leu Arg Leu
            355                 360                 365 ttc cca att gct atg aga ctt gag agg gtc tgc aaa aaa gat gtt gag    1215
Phe Pro Ile Ala Met Arg Leu Glu Arg Val Cys Lys Lys Asp Val Glu
        370                 375                 380 atc aat ggg atg ttc att ccc aaa ggg tgg gtg gtg atg att cca agc    1263
Ile Asn Gly Met Phe Ile Pro Lys Gly Trp Val Val Met Ile Pro Ser
    385                 390                 395 tat gct ctt cac cgt gac cca aag tac tgg aca gag cct gag aag ttc    1311
Tyr Ala Leu His Arg Asp Pro Lys Tyr Trp Thr Glu Pro Glu Lys Phe
400                 405                 410 ctc cct gaa aga ttc agc aag aag aac aag gac aac ata gat cct tac    1359
Leu Pro Glu Arg Phe Ser Lys Lys Asn Lys Asp Asn Ile Asp Pro Tyr
415                 420                 425                 430
```

-continued

```
ata tac aca ccc ttt gga agt gga ccc aga aac tgc att ggc atg agg      1407
Ile Tyr Thr Pro Phe Gly Ser Gly Pro Arg Asn Cys Ile Gly Met Arg
                435                 440                 445 ttt gct ctc atg aac atg aaa ctt gct cta atc aga gtc ctt cag aac      1455
Phe Ala Leu Met Asn Met Lys Leu Ala Leu Ile Arg Val Leu Gln Asn
        450                 455                 460 ttc tcc ttc aaa cct tgt aaa gaa aca cag atc ccc ctg aaa tta agc      1503
Phe Ser Phe Lys Pro Cys Lys Glu Thr Gln Ile Pro Leu Lys Leu Ser
    465                 470                 475 tta gga gga ctt ctt caa cca gaa aaa ccc gtt gtt cta aag gtt gag      1551
Leu Gly Gly Leu Leu Gln Pro Glu Lys Pro Val Val Leu Lys Val Glu
480                 485                 490 tca agg gat ggc acc gta agt gga gcc tga attttcctaa ggacttctgc        1601
Ser Arg Asp Gly Thr Val Ser Gly Ala
495                 500 tttgctcttc aagaaatctg tgcctgagaa caccagagac ctcaaattac tttgtgaata    1661
gaactctgaa atgaagatgg gcttcatcca atggactgca taaataaccg gggattctgt    1721
acatgcattg agctctctca ttgtctgtgt agagtgttat acttgggaat ataaggagg     1781 tgaccaaatc agtgtgagga ggtagatttg gctcctctgc ttctcacggg actatttcca   1841
ccacccccag ttagcaccat taactcctcc tgagctctga taagagaatc aacatttctc   1901
aataatttcc tccacaaatt attaatgaaa ataagaatta ttttgatggc tctaacaatg   1961
acatttatat cacatgtttt ctctggagta ttctatagtt ttatgttaaa tcaataaaga   2021
ccactttaca aaagtattat cagatgcttt cctgcacatt aaggagaatc tatagaactg   2081
aatgagaacc aacaagtaaa tattttggt cattgtaatc actgttggcg tggggccttt    2141
gtcagaacta gaattgatt attaacatag gtgaaagtta atccactgtg actttgccca    2201
ttgtttagaa agaatattca tagtttaatt atgccttttt tgatcaggca catggctcac   2261
gcctgtaatc ctagcagttt gggaggctga gccgggtgga tcgcctgagg tcaggagttc   2321
aagacaagcc tggcctacat ggtgaaaccc catctctact aaaaatacac aaattagcta   2381
ggcatggtgg actcgcctgt aatctcacta cacaggaggc tgaggcagga gaatcacttg   2441
aacctgggag gcggatgttg aagtgagctg agattgcacc actgcactcc agtctgggtg   2501
agagtgagac tcagtcttaa aaaaatatgc cttttgaag cacgtacatt ttgtaacaaa    2561
gaactgaagc tcttattata ttattagttt tgatttaatg ttttcagccc atctcctttc   2621
atatttctgg gagacagaaa acatgtttcc ctacacctct tgcttccatc ctcaacaccc   2681
aactgtctcg atgcaatgaa cacttaataa aaaacagtcg attggtcaaa aaaaaaaaa    2741 aaaaaaaaaa aagaattc                                                  2759
```

<210> SEQ ID NO 2
<211> LENGTH: 503
<212> TYPE: PRT
<213> ORGANISM: H. sapiens

<400> SEQUENCE: 2

```
Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60
```

-continued

```
His Lys Lys Tyr Gly Lys Val Trp Gly Phe Tyr Asp Gly Gln Gln Pro
 65                  70                  75                  80

Val Leu Ala Ile Thr Asp Pro Asp Met Ile Lys Thr Val Leu Val Lys
                 85                  90                  95

Glu Cys Tyr Ser Val Phe Thr Asn Arg Arg Pro Phe Gly Pro Val Gly
                100                 105                 110

Phe Met Lys Ser Ala Ile Ser Ile Ala Glu Asp Glu Glu Trp Lys Arg
            115                 120                 125

Leu Arg Ser Leu Leu Ser Pro Thr Phe Thr Ser Gly Lys Leu Lys Glu
        130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
                180                 185                 190

Ile Asp Ser Leu Asn Asn Pro Gln Asp Pro Phe Val Glu Asn Thr Lys
            195                 200                 205

Lys Leu Leu Arg Phe Asp Phe Leu Asp Pro Phe Phe Leu Ser Ile Thr
        210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
                260                 265                 270

Gln Leu Met Ile Asp Ser Gln Asn Ser Lys Glu Thr Glu Ser His Lys
            275                 280                 285

Ala Leu Ser Asp Leu Glu Leu Val Ala Gln Ser Ile Ile Phe Ile Phe
        290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
                340                 345                 350

Met Glu Tyr Leu Asp Met Val Val Asn Glu Thr Leu Arg Leu Phe Pro
            355                 360                 365

Ile Ala Met Arg Leu Glu Arg Val Cys Lys Lys Asp Val Glu Ile Asn
        370                 375                 380

Gly Met Phe Ile Pro Lys Gly Trp Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
                420                 425                 430

Thr Pro Phe Gly Ser Gly Pro Arg Asn Cys Ile Gly Met Arg Phe Ala
            435                 440                 445

Leu Met Asn Met Lys Leu Ala Leu Ile Arg Val Leu Gln Asn Phe Ser
        450                 455                 460

Phe Lys Pro Cys Lys Glu Thr Gln Ile Pro Leu Lys Leu Ser Leu Gly
465                 470                 475                 480
```

Gly Leu Leu Gln Pro Glu Lys Pro Val Val Leu Lys Val Glu Ser Arg
            485                 490                 495

Asp Gly Thr Val Ser Gly Ala
            500

<210> SEQ ID NO 3
<211> LENGTH: 1345
<212> TYPE: DNA
<213> ORGANISM: H. sapiens
<220> FEATURE:
<221> NAME/KEY: Other
<222> LOCATION: (0)...(0)

<400> SEQUENCE: 3

| | | | | | |
|---|---|---|---|---|---|
| ctgcagtgac | cactgcccca | tcattgctgg | ctgaggtggt | tggggtccat | ctggctatct | 60 |
| gggcagctgt | tctcttctct | cctttctctc | ctgtttccag | acatgcagta | tttccagaga | 120 |
| gaaggggcca | ctctttggca | agaacctgt | ctaacttgct | atctatggca | ggacctttga | 180 |
| agggttcaca | ggaagcagca | caaattgata | ctattccacc | aagccatcag | ctccatctca | 240 |
| tccatgccct | gtctctcctt | tagggtccc | cttgccaaca | gaatcacaga | ggaccagcct | 300 |
| gaaagtgcag | agacagcagc | tgaggcacag | ccaagagctc | tggctgtatt | aatgacctaa | 360 |
| gaagtcacca | gaaagtcaga | aggatgcata | gcagaggccc | agcaatctca | gctaagtcaa | 420 |
| ctccaccagc | ctttctagtt | gcccactgtg | tgtacagcac | cctggtaggg | accagagcca | 480 |
| tgacagggaa | taagactaga | ctatgcccct | gaggagctca | cctctgttca | gggaaacagg | 540 |
| cgtggaaaca | caatggtggt | aaagaggaaa | gaggacaata | ggattgcatg | aagggatgg | 600 |
| aaagtgccca | ggggaggaaa | tggttacatc | tgtgtgagga | gtttggtgag | gaaagactct | 660 |
| aagagaaggc | tctgtctgtc | tgggtttgga | aggatgtgta | ggagtcttct | aggggcaca | 720 |
| ggcacactcc | aggcataggt | aaagatctgt | aggtgtggct | tgttgggatg | aatttcaagt | 780 |
| attttggaat | gaggacagcc | atagagacaa | gggcargaga | gaggcgattt | aatagatttt | 840 |
| atgccaatgg | ctccacttga | gtttctgata | agaacccaga | accccttggac | tccccagtaa | 900 |
| cattgattga | gttgtttatg | atacctcata | gaatatgaac | tcaaaggagg | tcagtgagtg | 960 |
| gtgtgtgtgt | gattctttgc | caacttccaa | ggtggagaag | cctcttccaa | ctgcaggcag | 1020 |
| agcacaggtg | gccctgctac | tggctgcagc | tccagccctg | cctccttctc | tagcatataa | 1080 |
| acaatccaac | agcctcactg | aatcactgct | gtgcagggca | ggaaagctcc | atgcacatag | 1140 |
| cccagcaaag | agcaacacag | agctgaaagg | aagactcaga | ggagagagat | aagtaaggaa | 1200 |
| agtagtgatg | gctctcatcc | cagacttggc | catggaaacc | tggcttctcc | tggctgtcag | 1260 |
| cctggtgctc | ctctatctgt | gagtaactgt | tcaggctcct | cttctctgtt | tcttggactt | 1320 |
| ggggtcgtaa | tcaggcctct | ctttt | | | | 1345 |

<210> SEQ ID NO 4
<211> LENGTH: 591
<212> TYPE: DNA
<213> ORGANISM: H. sapiens
<220> FEATURE:
<221> NAME/KEY: Other
<222> LOCATION: (0)...(0)

<400> SEQUENCE: 4

| | | | | | |
|---|---|---|---|---|---|
| ggcttttgta | tgtttgacat | ggaatgtcat | aaaaagtatg | gaaaagtgtg | ggggtgagta | 60 |
| ttctggaaac | ttccattgga | tagacttgtt | tctatgatga | gtttacccca | ctgcacagag | 120 |
| gacagtctca | gcccaaagcc | tcttgggatg | aagctcttgt | caacctaact | acaaacagag | 180 |

-continued

```
agaagttctc tgaaagaaga agatatttat ttgggtgtag agtattgcaa tgggaatctg      240
catgccttta taaactatgt gcaaattcag ggaagtaaag caagacaaag aggctccaag      300
gaaaatatga aggaggattt cttatcagtt ttgaaataat tatccttcgc tacaaagatc      360
agtaacaagg gtgacgcctc accaaggttg gacaggcagt tgctgggcag gtgtccttgc      420
agaaatattt ttttaatgtt gggatggcct ttgtgcaagc ttgtatttg cggagtcttt      480 gtgatatttt gttatcaggc acacaagcat gagaatcctc tcttcatagc cttctttgat      540
ttatttgtca gggttttttac acacacacac acacacacac acacacacac a            591
```

<210> SEQ ID NO 5
<211> LENGTH: 433
<212> TYPE: DNA
<213> ORGANISM: H. sapiens
<220> FEATURE:
<221> NAME/KEY: Other
<222> LOCATION: (0)...(0)

<400> SEQUENCE: 5

```
catcacccag tagacagtca ctaaatagtt gttgaataag tgttcctgtt taacacattt      60
tctacaacca tggagacctc cacaactgat gtaggacaaa atgtttctgc tttsaactct     120
agccttttgg tccagtggga tttatgaaaa gtgccatctc tatagctgag gatgaagaat     180
ggaagagatt acgatcattg ctgtctccaa ccttcaccag tggaaaactc aaggaggtat     240
gaaaataaca tgagttttaa taagaaactt aagaatgaa tctggtgggg acaggtataa      300
aataagatca cagtcccttt ccaaggggta gtccactgaa tttgagctgc ctaaaaatgg     360
tcttttatct ttatgtacag aaaacacatc acaaaattca ttataaaatg tcacttactg     420
ctccatgctg ggg                                                        433
```

<210> SEQ ID NO 6
<211> LENGTH: 408
<212> TYPE: DNA
<213> ORGANISM: H. sapiens
<220> FEATURE:
<221> NAME/KEY: Other
<222> LOCATION: (0)...(0)

<400> SEQUENCE: 6

```
tctgcacatt taactatggg tggtgttgtg ttttgtgctt agatggtccc tatcattgcc      60
cagtatggag atgtgttggt gagaaatctg aggcgggaag cagagacagg caagcctgtc     120
accttgaaag agtaagtaga agcgcagcca tggggttctg agctgtcatg aacccctcca     180
gckgcctgcc atggagctga tattcctgct gttgggttat tccagtgacc agacaaaagg     240
agggctgtgg taatgcaact tcaatgggtc tcccaagatg gggcagctcc gatgaggagg     300
tggggcagct ggaggaaaag gatcttctcc cctgtgcaca ggggccaggg tttacatatc     360
cattaaattg tcaccttgga tattctagaa gactaaatat atccttta                  408
```

<210> SEQ ID NO 7
<211> LENGTH: 429
<212> TYPE: DNA
<213> ORGANISM: H. sapiens
<220> FEATURE:
<221> NAME/KEY: Other
<222> LOCATION: (0)...(0)

<400> SEQUENCE: 7

```
ttttaatttt ccacatcttt ctccactcag cgtctttggg gcctacagca tggatgtgat      60
```

-continued

| | | |
|---|---|---|
| cactagcaca tcatttggag tgaacatyga ctctctcaac aatccacaag acccctttgt | 120 |
| ggaaaacacc aagaagcttt taagatttga ttttttggat ccattctttc tctcaataag | 180 |
| tatgtggact actatttcct tttatttatc ttkctctctt aaaaataact gctttattga | 240 |
| gatataaatc accatgtaat tcatccactt aaaatataca gttcagtgat ttgtagtaca | 300 |
| tttgaagata tgtgtgacca tcatcatttt aaactttaaa acttttttg tcaatctaga | 360 |
| gacctcatac attttagct atcagccccc tgtcacaaac cctgtcatca tatgcaacca | 420 |
| ctaatcaac | 429 |

<210> SEQ ID NO 8
<211> LENGTH: 352
<212> TYPE: DNA
<213> ORGANISM: H. sapiens
<220> FEATURE:
<221> NAME/KEY: Other
<222> LOCATION: (0)...(0)

<400> SEQUENCE: 8

| | | |
|---|---|---|
| aattgctttt ctattctttt cccttaggga tttgagggct tcacttagat ttctcttcat | 60 |
| ctaaactgtg atgccctaca ttgatctgat ttacctaaaa tgtctttcct ctcctttcag | 120 |
| ctctgtccga tctggagctc gtggcccaat caattatctt tattttgct ggctatgaaa | 180 |
| ccacgagcag tgttctctcc ttcattatgt atgaactggc cactcaccct gatgtccagc | 240 |
| agaaactgca ggaggaaatt gatgcagttt tacccaataa ggtgagtgga tgrtacatgg | 300 |
| agaaggaggg aggaggtgaa accttagcaa aaatgcctcc tcaccacttc cc | 352 |

<210> SEQ ID NO 9
<211> LENGTH: 309
<212> TYPE: DNA
<213> ORGANISM: H. sapiens
<220> FEATURE:
<221> NAME/KEY: Other
<222> LOCATION: (0)...(0)

<400> SEQUENCE: 9

| | | |
|---|---|---|
| gcatagcagg atttcaatga ccagcccaca aaagtatcct gtgtactact agttgagggg | 60 |
| tggcccctaa gtaagaaacc ctaacatgta actcttaggg gtattatgtc attaactttt | 120 |
| taaaaatcta ccaaygtgga accagattca gcaagaagaa caaggacaac atagatcctt | 180 |
| acatatacac acccttttgga agtggaccca gaaactgcat tggcatgagg tttgctctca | 240 |
| tgaacatgaa acttgctcta atcagagtcc ttcagaactt ctccttcaaa ccttgtaaag | 300 |
| aaacacagg | 309 |

<210> SEQ ID NO 10
<211> LENGTH: 24
<212> TYPE: DNA
<213> ORGANISM: H. sapiens

<400> SEQUENCE: 10

| | | |
|---|---|---|
| tggcttgttg ggatgaattt caag | 24 |

<210> SEQ ID NO 11
<211> LENGTH: 24
<212> TYPE: DNA
<213> ORGANISM: H. sapiens

<400> SEQUENCE: 11

| | | |
|---|---|---|
| ttactgggga gtccaagggt tctg | 24 |

<210> SEQ ID NO 12
<211> LENGTH: 32
<212> TYPE: DNA
<213> ORGANISM: H. sapiens

<400> SEQUENCE: 12
ttaaatcgcc tctctcttgc ccttgtctct at                                    32

<210> SEQ ID NO 13
<211> LENGTH: 29
<212> TYPE: DNA
<213> ORGANISM: H. sapiens

<400> SEQUENCE: 13
aatcgcctct ctcctgccct tgtctctat                                        29

<210> SEQ ID NO 14
<211> LENGTH: 17
<212> TYPE: DNA
<213> ORGANISM: H. sapiens

<400> SEQUENCE: 14
tgaggagttt ggtgagg                                                     17

<210> SEQ ID NO 15
<211> LENGTH: 18
<212> TYPE: DNA
<213> ORGANISM: H. sapiens

<400> SEQUENCE: 15
caagaaacag agaagagg                                                    18

<210> SEQ ID NO 16
<211> LENGTH: 17
<212> TYPE: DNA
<213> ORGANISM: H. sapiens

<400> SEQUENCE: 16
cccacacaaa tacatcc                                                     17

<210> SEQ ID NO 17
<211> LENGTH: 17
<212> TYPE: DNA
<213> ORGANISM: H. sapiens

<400> SEQUENCE: 17
agaagacatg gctttcc                                                     17

<210> SEQ ID NO 18
<211> LENGTH: 17
<212> TYPE: DNA
<213> ORGANISM: H. sapiens

<400> SEQUENCE: 18
tgtcacttac tgctcca                                                     17

<210> SEQ ID NO 19
<211> LENGTH: 16
<212> TYPE: DNA
<213> ORGANISM: H. sapiens

<400> SEQUENCE: 19
caacaggaaa cccaca                                                      16

```
<210> SEQ ID NO 20
<211> LENGTH: 18
<212> TYPE: DNA
<213> ORGANISM: H. sapiens

<400> SEQUENCE: 20
tccacaatca atacatgc                                                 18

<210> SEQ ID NO 21
<211> LENGTH: 15
<212> TYPE: DNA
<213> ORGANISM: H. sapiens

<400> SEQUENCE: 21
cctgaagcca gcaga                                                    15

<210> SEQ ID NO 22
<211> LENGTH: 20
<212> TYPE: DNA
<213> ORGANISM: H. sapiens

<400> SEQUENCE: 22
catctcaaca agactgaaag                                               20

<210> SEQ ID NO 23
<211> LENGTH: 18
<212> TYPE: DNA
<213> ORGANISM: H. sapiens

<400> SEQUENCE: 23
tgaactccag aactgaag                                                 18

<210> SEQ ID NO 24
<211> LENGTH: 18
<212> TYPE: DNA
<213> ORGANISM: H. sapiens

<400> SEQUENCE: 24
ggcttttgta tgtttgac                                                 18

<210> SEQ ID NO 25
<211> LENGTH: 16
<212> TYPE: DNA
<213> ORGANISM: H. sapiens

<400> SEQUENCE: 25
cggtttgtga agacag                                                   16

<210> SEQ ID NO 26
<211> LENGTH: 18
<212> TYPE: DNA
<213> ORGANISM: H. sapiens

<400> SEQUENCE: 26
ccttggggaa aactggat                                                 18

<210> SEQ ID NO 27
<211> LENGTH: 16
<212> TYPE: DNA
<213> ORGANISM: H. sapiens

<400> SEQUENCE: 27
ctcctgggaa gtggtg                                                   16
```

```
<210> SEQ ID NO 28
<211> LENGTH: 17
<212> TYPE: DNA
<213> ORGANISM: H. sapiens

<400> SEQUENCE: 28
tgaggagttt ggtgagg                                                    17

<210> SEQ ID NO 29
<211> LENGTH: 18
<212> TYPE: DNA
<213> ORGANISM: H. sapiens

<400> SEQUENCE: 29
caagaaacag agaagagg                                                   18

<210> SEQ ID NO 30
<211> LENGTH: 18
<212> TYPE: DNA
<213> ORGANISM: H. sapiens

<400> SEQUENCE: 30
gtgagtggtg tgtgtgtg                                                   18

<210> SEQ ID NO 31
<211> LENGTH: 18
<212> TYPE: DNA
<213> ORGANISM: H. sapiens

<400> SEQUENCE: 31
gtgattcagt gaggctgt                                                   18

<210> SEQ ID NO 32
<211> LENGTH: 21
<212> TYPE: DNA
<213> ORGANISM: H. sapiens

<400> SEQUENCE: 32
gggataaatc tctattgagc a                                               21

<210> SEQ ID NO 33
<211> LENGTH: 17
<212> TYPE: DNA
<213> ORGANISM: H. sapiens

<400> SEQUENCE: 33
gctttcctca gcatgga                                                    17

<210> SEQ ID NO 34
<211> LENGTH: 17
<212> TYPE: DNA
<213> ORGANISM: H. sapiens

<400> SEQUENCE: 34
tgtcacttac tgctcca                                                    17

<210> SEQ ID NO 35
<211> LENGTH: 17
<212> TYPE: DNA
<213> ORGANISM: H. sapiens

<400> SEQUENCE: 35
cacaggggag aagatcc                                                    17
```

```
<210> SEQ ID NO 36
<211> LENGTH: 18
<212> TYPE: DNA
<213> ORGANISM: H. sapiens

<400> SEQUENCE: 36
tgtctgtctg gactggac                                              18

<210> SEQ ID NO 37
<211> LENGTH: 19
<212> TYPE: DNA
<213> ORGANISM: H. sapiens

<400> SEQUENCE: 37
aaaatgatga tggtcacac                                             19

<210> SEQ ID NO 38
<211> LENGTH: 21
<212> TYPE: DNA
<213> ORGANISM: H. sapiens

<400> SEQUENCE: 38
tagtgtcagg agagtagaaa g                                          21

<210> SEQ ID NO 39
<211> LENGTH: 18
<212> TYPE: DNA
<213> ORGANISM: H. sapiens

<400> SEQUENCE: 39
gcctaattga ttctttgg                                              18

<210> SEQ ID NO 40
<211> LENGTH: 18
<212> TYPE: DNA
<213> ORGANISM: H. sapiens

<400> SEQUENCE: 40
atttgcctta ttctggtt                                              18

<210> SEQ ID NO 41
<211> LENGTH: 16
<212> TYPE: DNA
<213> ORGANISM: H. sapiens

<400> SEQUENCE: 41
ctcctgggaa gtggtg                                                16

<210> SEQ ID NO 42
<211> LENGTH: 18
<212> TYPE: DNA
<213> ORGANISM: H. sapiens

<400> SEQUENCE: 42
ggcttttgta tgtttgac                                              18

<210> SEQ ID NO 43
<211> LENGTH: 19
<212> TYPE: DNA
<213> ORGANISM: H. sapiens

<400> SEQUENCE: 43
acaagggcaa gagagaggc                                             19
```

```
<210> SEQ ID NO 44
<211> LENGTH: 19
<212> TYPE: DNA
<213> ORGANISM: H. sapiens

<400> SEQUENCE: 44
acaagggcag gagagaggc                                                    19

<210> SEQ ID NO 45
<211> LENGTH: 9
<212> TYPE: DNA
<213> ORGANISM: H. sapiens

<400> SEQUENCE: 45 gggttttta                                                                9

<210> SEQ ID NO 46
<211> LENGTH: 41
<212> TYPE: DNA
<213> ORGANISM: H. sapiens

<400> SEQUENCE: 46 gggttttac acacacacac acacacacac acacacacac a                            41

<210> SEQ ID NO 47
<211> LENGTH: 19
<212> TYPE: DNA
<213> ORGANISM: H. sapiens

<400> SEQUENCE: 47
ttctgctttg aactctagc                                                    19

<210> SEQ ID NO 48
<211> LENGTH: 19
<212> TYPE: DNA
<213> ORGANISM: H. sapiens

<400> SEQUENCE: 48
ttctgctttc aactctagc                                                    19

<210> SEQ ID NO 49
<211> LENGTH: 19
<212> TYPE: DNA
<213> ORGANISM: H. sapiens

<400> SEQUENCE: 49
ccctccagct gcctgccat                                                    19

<210> SEQ ID NO 50
<211> LENGTH: 19
<212> TYPE: DNA
<213> ORGANISM: H. sapiens

<400> SEQUENCE: 50
ccctccagcg gcctgccat                                                    19

<210> SEQ ID NO 51
<211> LENGTH: 19
<212> TYPE: DNA
<213> ORGANISM: H. sapiens

<400> SEQUENCE: 51
agtgaacatc gactctctc                                                    19
```

```
<210> SEQ ID NO 52
<211> LENGTH: 19
<212> TYPE: DNA
<213> ORGANISM: H. sapiens

<400> SEQUENCE: 52
agtgaacatt gactctctc                                              19

<210> SEQ ID NO 53
<211> LENGTH: 19
<212> TYPE: DNA
<213> ORGANISM: H. sapiens

<400> SEQUENCE: 53
atttatcttt ctctcttaa                                              19

<210> SEQ ID NO 54
<211> LENGTH: 19
<212> TYPE: DNA
<213> ORGANISM: H. sapiens

<400> SEQUENCE: 54
atttatcttg ctctcttaa                                              19

<210> SEQ ID NO 55
<211> LENGTH: 19
<212> TYPE: DNA
<213> ORGANISM: H. sapiens

<400> SEQUENCE: 55
gagtggatgg tacatggag                                              19

<210> SEQ ID NO 56
<211> LENGTH: 19
<212> TYPE: DNA
<213> ORGANISM: H. sapiens

<400> SEQUENCE: 56
gagtggatga tacatggag                                              19

<210> SEQ ID NO 57
<211> LENGTH: 18
<212> TYPE: DNA
<213> ORGANISM: H. sapiens

<400> SEQUENCE: 57
tctaccaacg tggaacca                                               18

<210> SEQ ID NO 58
<211> LENGTH: 18
<212> TYPE: DNA
<213> ORGANISM: H. sapiens

<400> SEQUENCE: 58
tctaccaatg tggaacca                                               18
```

ISOLATED CYP3A4 NUCLEIC ACID MOLECULES AND DETECTION METHODS

This application claims priority under 35 U.S.C. §119(e) from U.S. Provisional Application Ser. No. 60/058,612, filed Sep. 10, 1997. The entire disclosure of U.S. Provisional Application Ser. No. 60/058,612 is incorporated herein by reference.

INTRODUCTION

Cytochrome P450 enzymes are a heme-containing family that play central roles in oxidative, peroxidative and reductive metabolism of numerous endogenous and exogenous compounds, including many pharmaceutical agents. Substances known to be metabolized by P450 enzymes include steroids, bile acids, fatty acids, prostaglandins, leukotrienes, biogenic amines, retinoids, lipid hydroperoxides, phytoalexins, pharmaceuticals, environmental chemicals and pollutants. P450 substrates also include natural plant products involved in flavor, odor, flower color, and the response to wounding. P450 enzymes and other drug-metabolizing enzymes maintain steady-state levels of endogenous ligands involved in ligand-modulated transcription of genes effecting growth, apoptosis, differentiation, cellular homeostasis, and neuroendocrine functions. The metabolism of foreign chemicals by P450 enzymes can produce toxic metabolites, some of which have been implicated as agents responsible for birth defects and tumor initiation and progression.

The P450 gene superfamily is likely to have evolved from an ancestral gene present before the prokaryote/eukaryotedivergence. The number of individual P450 genes in any mammalian species is estimated at 60 to 200. The CYP2C and CYP3A subfamilies are unique in that they are present in large amounts in human liver microsomes, and there are many forms in each subfamily. Several human cDNAs encoding CYP3A proteins have been identified. The most important of these are CYP3A4, CYP3A5 and CYP3A7. CYP3A4 and CYP3A7 genes are 87% homologous by amino acid and 95% homologous by nucleotide sequence, while CYP3A4 and CYP3A5 are only 88% homologous in the coding region. CYP3A4 and CYP3A7 are 91% homologous in the 5'-flanking sequences, differing by the presence of a unique P450NF specific element (NFSE) and a P450HFLa specific element (HFLaSE), respectively (Hashimoto et al, 1993).

It has been shown that polymorphisms in the CYP2D6 gene correlates with enzyme activity measured by phenotyping with dextromethorphan or debrisoquine (Sachse et al. (1997) Am. J. Hum. Genet. 60:248–295).

The CYP3A subclass catalyzes a remarkable number of oxidation reactions of clinically important drugs such as quinidine, warfarin, erythromycin, cyclosporin A, midazolam, lidocain, nifedipine, and dapsone. Current estimates are that more than 60% of clinically used drugs are metabolized by the CYP3A4 enzyme, including such major drug classes as calcium channel blockers, immunosuppressors, macrolide antibiotics and anticancer drugs, see Brian et al. (1990) Biochemistry 29:11280–11292.

Expression profiles for each member of this family varies significantly. CYP3A4 is expressed in all adult human liver and intestine, accounting for more than 50% of total P450 in both organs. Expression is inducible in vivo and in vitro by numerous compounds such as rifampicin, barbiturates and glucocorticoids. In kidney, CYP3A4 is expressed polymorphically. CYP3A4 expression is sex-influenced, as females have 24% greater expression than males. CYP3A5 is detected in 10–30% of Caucasian adult livers, and expressed constitutively in adult kidney. CYP3A5 expression does not appear to be sex-influenced and only moderately inducible by xenobiotics both in vivo and in vitro. CYP3A7 is expressed in fetal liver but only in 25% of adult livers. Molecular mechanisms responsible for the developmentally specific expression of CYP3A's are unknown.

Since the rates of metabolism of drugs, toxins, etc. can depend on the amounts and kinds of P450s expressed in a tissue, variation in biological response may be determined by the profile of expression of P450s in each person. Analysis of genetic polymorphisms that lead to altered expression and enzyme activity are therefore of interest.

SUMMARY OF THE INVENTION

Genetic sequence polymorphisms are identified in the human CYP3A4 gene. Nucleic acids comprising the polymorphic sequences are used in screening assays, and for genotyping individuals. The genotyping information is used to predict the rate of metabolism for CYP3A4 substrates, and the effect that CYP3A4 modulators will have on such metabolism. The information allows better prediction of drug interactions, and effective dose for an individual.

DATABASE REFERENCES FOR NUCLEOTIDE SEQUENCES

Genbank accession no. S74700 provides the CYP3A5 5' genomic region. Genbank accession no. D11131 provides a partial sequence of the human cytochrome P450IIIA4 gene. Genbank accession no. M18907 (cDNA) provides the cDNA sequence of a human CYP3A4 allele. Sequences of the CYP3A4 gene are provided in the SEQLIST as follows: cDNA sequence as SEQ ID NO:1, the encoded polypeptide as SEQ ID NO:2, the promoter region as SEQ ID NO:3, intron 3 as SEQ ID NO:4, intron 4 as SEQ ID NO:5, intron 6 as SEQ. ID NO:6, exon 7, intron 7 as SEQ ID NO:7, intron 10as SEQ ID NO:8, intron 11 as SEQ ID NO:9.

DESCRIPTION OF THE SPECIFIC EMBODIMENTS

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. Relationships between polymorphisms in metabolic enzymes or drug targets and both response and toxicity can be used to optimize therapeutic dose administration.

Genetic polymorphisms are identified in the human CYP3A4 gene. Nucleic acids comprising the polymorphic sequences are used to screen patients for altered metabolism for CYP3A4 substrates, potential drug-drug interactions, and adverse/side effects, as well as diseases that result from environmental or occupational exposure to toxins. The nucleic acids are used to establish animal, cell culture and in vitro cell-free models for drug metabolism.

DEFINITIONS

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a construct" includes a plurality of such constructs and reference to "the CYP3A4 nucleic acid" includes reference to one or more nucleic acids and equivalents thereof known to those skilled in the art, and so forth. All technical and scientific terms used herein have the same meaning as commonly understood to one of ordinary skill in the art to which this invention belongs unless clearly indicated otherwise.

CYP3A4 Polymorphic Sequences. It has been found that, specific sites in the CYP3A4 gene sequence are polymorphic, i.e. within a population, more than one nucleotide (G, A, T, C) is found at a specific position. Polymorphisms may provide functional differences in the genetic sequence, through changes in the encoded polypeptide, changes in mRNA stability, binding of transcriptional and translation factors to the DNA or RNA, and the like. The polymorphisms are also used as single nucleotide polymorphisms (SNPs) to detect genetic linkage to phenotypic variation in activity and expression of the particular protein.

SNPs are generally biallelic systems, that is, there are two alleles that an individual may have for any particular marker. SNPs, found approximately every kilobase, offer the potential for generating very high density genetic maps, which will be extremely useful for developing haplotyping systems for genes or regions of interest, and because of the nature of SNPs, they may in fact be the polymorphisms associated with the disease phenotypes under study. The low mutation rate of SNPs also makes them excellent markers for studying complex genetic traits.

In order to provide an unambiguous identification of the specific site of a polymorphism, sequences flanking the polymorphic site are shown in the tables, where the 5' and 3' flanking sequence is non-polymorphic, and the central position, shown in bold, is variable. It will be understood that there is no special significance to the length of non-polymorphic flanking sequence that is included, except to aid in positioning the polymorphism in the genomic sequence.

The sequence of at least one allele of human CYP3A4 is known in the art, and accessible in public databases, as cited above. This sequence is useful as a reference for the genomic location of the human gene, and for specific coding region sequences. The subject polymorphic sequences are provided in Table 3, and include the CYP3A4-A392/CYP3A4-G392 alternative forms, which are associated with differences in expression level of the polypeptide. As used herein, the term "CYP3A4 gene" is intended to refer to both the wild-type and variant sequences, unless specifically denoted otherwise.

Nucleic acids of particular interest comprise, the provided variant nucleotide sequence(s). For screening purposes, hybridization probes may be used where both polymorphic forms are present, either in separate reactions, or labeled such that they can be distinguished from each other. Assays may utilize nucleic acids that hybridize to one or more of the described polymorphisms.

The genomic CYP3A4 sequence, including specific transcriptional and translational regulatory sequences, such as promoters, enhancers, etc., including about 1 kb, but possibly more, of flanking genomic DNA at the 5' end of the transcribed region, is of particular interest. The promoter region is useful for determining the pattern of CYP3A4 expression, e.g. induction and inhibition of expression in various tissues, and for providing promoters that mimic these native patterns of expression. A polymorphic CYP3A4 gene sequence, i.e. including one or more of the provided polymorphisms, is useful for expression studies to determine the effect of promoter and/or intron sequence variations on mRNA expression and stability. The polymorphisms are also used as single nucleotide polymorphisms to detect genetic linkage to phenotypic variation in activity and expression of CYP3A4.

As used herein, the term "CYP3A4 gene" is intended to generically refer to both the wild-type (reference) and variant forms of the sequence, unless specifically denoted otherwise. As it is commonly used in the art, the term "gene" is intended to refer to the genomic region encompassing the 5' UTR, exons, introns, and the 3' UTR. Individual segments may be specifically referred to, e.g. exon 2, intron 5, etc. Combinations of such segments that provide for a complete protein may be referred to generically as a protein coding sequence.

The promoter region of CYP3A4 contains a number of sequence motifs for binding transcription regulatory factors. These include a basic transcription element (SEQ ID NO:1, nt. 1054–1071); octamer motif (SEQ ID NO:1, nt. 975–982); TATA box (SEQ ID NO:1, nt. 1075–1081); HNF-5 site (SEQ ID NO:1, nt. 913–920); estrogen responsive elements (SEQ ID NO:1, nt. 735–750, 895–908); CAAT box (SEQ ID NO:1, nt. 843–848); p53 binding site (SEQ ID NO:1, nt. 721–735); AP-3 binding site (SEQ ID NO:1, nt. 682–693); NFSE site (SEQ ID NO:1, nt. 810–819); and progesterone/glucocorticoid responsive element (SEQ ID NO:1, nt.870–883). Regulatory sequences can be used to identify trans acting factors that regulate or mediate CYP3A4 expression.

Fragments of the DNA sequence are obtained by chemically synthesizing oligonucleotides in accordance with conventional methods, by restriction enzyme digestion, by PCR amplification, etc. For the most part, DNA fragments will be of at least 15 nt, usually at least 20 nt, often at least 50 nt. Such small DNA fragments are useful as primers for PCR, hybridization screening, etc. Larger DNA fragments, i.e. greater than 100 nt are useful for production of the encoded polypeptide, promoter motifs, etc. For use in amplification reactions, such as PCR, a pair of primers will be used. The exact composition of primer sequences is not critical to the invention, but for most applications, the primers will hybridize to the subject sequence under stringent conditions, as known in the art.

The CYP3A4 nucleic acid sequences are isolated and obtained in substantial purity, generally as other than an intact mammalian chromosome. Usually, the DNA will be obtained substantially free of other nucleic acid sequences that do not include a CYP3A4 sequence or fragment thereof, generally being at least about 50%, usually at least about 90% pure and are typically "recombinant", i.e. flanked by one or more nucleotides with which it is not normally associated on a naturally occurring chromosome.

CYP3A4 Polypeptides. The CYP3A4 genetic sequence, including polymorphisms, may be employed for synthesis of a complete CYP3A4 protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host. The polypeptides may be expressed in prokaryotes or eukaryotes in accordance with conventional ways, depending upon the purpose for expression. Small peptides can also be synthesized in the laboratory.

Substrate: a chemical entity that is modified by CYP3A4 oxidation, usually under normal physiological conditions. Most of these substrates are lipophilic compounds. Although the duration of drug action tends to be shortened by metabolic transformation, drug metabolism is not "detoxification". Frequently the metabolic product has greater biologic activity than the drug itself. In some cases the desirable pharmacologic actions are entirely attributable to metabolites, the administered drugs themselves being inert. Likewise, the toxic side effects of some drugs may be due in whole or in part to metabolic products.

The range of known substrates for CYP3A4 is very broad, including steroids, e.g. testoterone, estradiol, mifepristone; tricyclic antidepressants, e.g. amitriptyline, clomipramine, imipramine, desipramine; SSRI, e.g. citalopram, fluoxetine, fluvoxamine, paroxetine and sertralin; bile acids; protease inhibitors, e.g. saquinovir, indinavir; fatty acids; prostaglandins; leukotrienes; biogenic amines; retinoids; lipid hydroperoxides; phytoalexins; antibiotics, e.g. erythromycin; taxanes, e.g. paclitaxel, docetaxel; anti-hypertensives, e.g. diltiazem; environmental chemicals and pollutants, felodipine, rifabutin, haloperidol, triazolam, terfenadine, lovastatin, chlorzoxazone, alprazolam, etc.

Modifier. A chemical agent that modulates the action of CYP3A4, either through altering its enzymatic activity (enzymatic modifier) or through modulation of expression (expression modifier). In some cases the modifier may also be a substrate, thereby inducing its own demise. Selective inhibitors of CYP3A4 include ketoconazole and troleandomycin. Other P450 selective inhibitors include venlafaxine, clarithromycin, fluconazole, itraconazole, ritonavir, orphenadrine, methimazole, midazolam, gestodene, etc. Recent studies have shown that orally administered grapefruit juice is an expression modifier of CYP3A4, acting to specifically down-regulate expression in enterocytes (Lown et al. (1997) *J. Clin. Invest* 99:2545–2553).

Recent studies (Schuetz and Schuetz (1996) *Mol Pharmacol* 49:311–318) on expression of P-glycoprotein and CYP3A4 showed that both proteins were up-regulated after treatment with many drugs, including rifampicin phenobarbital, clotrimazole, reserpine, and isosafrole. P-glycoprotein was up-regulated by midazolam and nifedipine, whereas CYP3A4 was not. Azoles appear to be broad spectrum inhibitors of cytochromes P450.

Pharmacokinetic Parameters. Pharmacokinetic parameters provide fundamental data for designing safe and effective dosage regimens. A drug's volume of distribution, clearance, and the derived parameter, half-life, are particularly important, as they determine the degree of fluctuation between a maximum and minimum plasma concentration during a dosage interval, the magnitude of steady state concentration and the time to reach steady state plasma concentration upon chronic dosing. The pharmacokinetics of drugs often vary considerably between individuals, largely because of variations in the expression of CYP enzymes in the liver and other tissues. Parameters derived from in vivo drug administration are useful in determining the clinical effect of a particular CYP3A4 genotype.

Expression assay. An assay to determine the effect of a sequence polymorphism on CYP3A4 expression. Expression assays may be performed in cell-free extracts, or by transforming cells with a suitable vector. Alterations in expression may occur in the basal level that is expressed in one or more cell types, or in the effect that an expression modifier has on the ability of the gene to be inhibited or induced. Expression levels of a variant alleles are compared by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like. Specific constructs for determining promoter strength of CYP3A4 are described in Hashimoto et al. (1993) *Eur. J. Biochem.* 218:585–595.

Gel shift or electrophoretic mobility shift assay provides a simple and rapid method for detecting DNA-binding proteins (Ausubel, F. M. et al. (1989). In: Current Protocols in Molecular Biology, Vol. 2, John Wiley and Sons, New York). This method has been used widely in the study of sequence-specific DNA-binding proteins, such as transcription factors. The assay is based on the observation that complexes of protein and DNA migrate through a nondenaturing polyacrylamide gel more slowly than free DNA fragments or double-stranded oligonucleotides. The gel shift assay is performed by incubating a purified protein, or a complex mixture of proteins (such as nuclear or cell extract preparations), with an end-labeled DNA fragment containing the putative protein binding site. The reaction products are then analyzed on a nondenaturing polyacrylamide gel. The specificity of the DNA-binding protein for the putative binding site is established by competition experiments using DNA fragments or oligonucleotides containing a binding site for the protein of interest, or other unrelated DNA sequences.

CYP3A4 is known to be expressed in liver, e.g. embryonic liver, mature hepatocytes; duodenal tissue, e.g. mucosal epithelial cells; and other epithelial cells throughout the digestive tract; breast tissue; placental tissue; lung tissue, e.g. bronchial glands, bronchiolar columnar and terminal epithelium, type II alveolar epithelium and alveolar macrophages, etc. Hepatic levels of CYP3A4 can be estimated by an erythromycin breath test, and vary by at least 10-fold among patients.

Substrate Screening Assay. Assays to determine the metabolic activity of a CYP3A4 protein or peptide fragment on a substrate. Many suitable assays are known in the art, including the use of primary or cultured cells, e.g. epithelial cells from liver, intestine, etc., genetically modified cells where the native CYP3A4 alleles are altered or inactivated, cell-free systems, e.g. microsomal preparations or recombinantly produced enzymes in a suitable buffer, or in animals, including human clinical trials. Clinical trials may monitor serum, urine, etc. levels of the substrate or its metabolite(s).

Typically a candidate-substrate is input into the assay system, and the oxidation to a metabolite is measured over time. The choice of detection system is determined by the substrate and the specific assay parameters. Assays are conventionally run, and will include negative and positive controls, varying concentrations of substrate and enzyme, etc.

Genotyping: CYP3A4 genotyping is performed by DNA or RNA sequence and/or hybridization analysis of any convenient sample from a patient, e.g. biopsy material, blood sample, scrapings from cheek, etc. A nucleic acid sample from an individual is analyzed for the presence of polymorphisms in CYP3A4, particularly those that affect the activity or expression of CYP3A4. Specific sequences of interest include any polymorphism that leads to changes in basal expression in one or more tissues, to changes in the modulation of CYP3A4 expression by modifiers, or alterations in CYP3A4 substrate specificity and/or activity.

Linkage Analysis: Diagnostic screening may be performed for polymorphisms that are genetically linked to a phenotypic variant in CYP3A4 activity or expression, particularly through the use of microsatellite markers or single nucleotide polymorphisms (SNP). The microsatellite or SNP polymorphism itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium.

Linkage analysis may be performed alone, or in combination with direct detection of phenotypically evident polymorphisms. The use of microsatellite markers for genotyping is well documented. For examples, see Mansfield et al. (1994) *Genomics* 24:225–233; and Ziegle et al. (1992) *Genomics* 14:1026–1031. The use of SNPs for genotyping is illustrated in Golevleva et al. (1996) *Am. J. Hum. Genet.* 59:570–578; and in Underhill et al. (1996) *P.N.A.S.* 93:196–200.

Transgenic Animal. The subject nucleic acids can be used to generate genetically modified non-human animals or site specific gene modifications in cell lines. The term "transgenic" is intended to encompass genetically modified animals having a deletion or other knock-out of CYP3A4 gene activity, having an exogenous CYP3A4 gene that is stably transmitted in the host cells; or having an exogenous CYP3A4 promoter operably linked to a reporter gene. Transgenic animals may be made through homologous recombination, where the CYP3A4 locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Genetically Modified Cells. Primary or cloned cells and cell lines are modified by the introduction of vectors comprising CYP3A4 gene polymorphisms. The gene may comprise one or more variant sequences, preferably a haplotype of commonly occurring combinations. U.S. Pat. No. 5,429, 948, Jul. 4, 1995 describes the construction and use of a cell line that expresses multiple P450 enzymes.

Vectors useful for introduction of the gene include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

The expression vector will have a transcriptional initiation region oriented to produce functional mRNA, preferably the native transcriptional initiation region, e.g. including the polymorphism described in Table 3. Generally the vectors will include markers for selection, and may also comprise detectable markers operably linked to the CYP3A4 promoter, transcription cassettes for internal controls, etc.

Cell-free Assay Systems. A number of cell-free assays have been described that are useful in the subject invention. Yamazaki et al. (1997) Arch Biochem Biophys 342:329–337 demonstrates reconstituted systems with recombinantly produced CYP3A4. U.S. Pat. No. 5,413,915 describes microsomal P450 oxidase enzyme complex dispersed in a thin film of a generally neutral hydrophilic film-forming binder. Substrates are converted into metabolic intermediates that can be detected by a calorimetric indicator present in the binder film or an adjacent binder film and undergoing a visible color change. U.S. Pat. No. 5,478,723 discloses methods for determining the enzyme or enzymes in the human body that metabolize a particular drug by comparing microsomal fractions from different donors.

GENOTYPING METHODS

The effect of a polymorphism in CYP3A4 gene sequence on the response to a particular substrate or modifier of CYP3A4 is determined by in vitro or in vivo assays. Such assays may include monitoring the metabolism of a substrate during clinical trials to determine the CYP3A4 enzymatic activity, specificity or expression level. Generally, in vitro assays are useful in determining the direct effect of a particular polymorphism, while clinical studies will also detect an enzyme phenotype that is genetically linked to a polymorphism.

The response of an individual to the substrate or modifier can then be predicted by determining the CYP3A4 genotype, with respect to the polymorphism. Where there is a differential distribution of a polymorphism by racial background, guidelines for drug administration can be generally tailored to a particular ethnic group.

The polymorphisms in the sequence of CYP3A4 provided in Table 3, particularly the A to G substitution at −392, are screened for the effect of the polymorphism on expression. Several effects are of interest, including basal expression levels in different tissues, alterations in enzyme activity or specificity, and the induction or inhibition of expression by modifiers. The latter is of particular interest in determining drug-drug interactions. In particular, pharmacokinetic drug interactions with antimicrobials are common because of the tendency to prescribe them in combination with other therapies.

Tissue specific differences in expression are of interest because the metabolism of drugs can vary with the route of administration. For example, certain orally administered drugs are affected by the CYP3A4 expression level in enterocytes, while the same drug administered intravenously is only affected by hepatic expression levels of CYP3A4.

The basal expression level in different tissue may be determined by analysis of tissue samples from individuals typed for the presence or absence, of a specific polymorphism. For example, the CYP3A4 mRNA or protein level in hepatocytes, gastrointestinal epithelial, etc. is determined. Any convenient method may be use, e.g.

ELISA, RIA, etc. for protein quantitation, northern blot or other hybridization analysis, quantitative RT-PCR, etc. for mRNA quantitation. The tissue specific expression is correlated with the genotype.

Alternatively, basal expression levels are determined by expression assays for the particular promoter sequence, as previously described. The assays may be performed with the CYP3A4 coding sequence or with a detectable marker sequence. To determine tissue specificity the assay is performed in cells derived from different sources.

The alteration of CYP3A4 expression in response to a modifier is determined by administering or combining the candidate modifier with an expression system, e.g. animal, cell, in vitro transcription assay, etc. The effect of the modifier on CYP3A4 transcription and/or steady state mRNA levels is determined. As with the basal expression levels, tissue specific interactions are of interest. Correlations are made between the ability of an expression modifier to affect CYP3A4 activity, and the presence of the provided polymorphisms. A panel of different modifiers, cell types, etc. may be screened in order to determine the effect under a number of different conditions.

A CYP3A4 polymorphism that results in altered enzyme activity or specificity is determined by a variety of assays known in the art. The enzyme may be tested for metabolism of a substrate in vitro, for example in defined buffer, or in cell or subcellular lysates, where the ability of a substrate to be oxidized by CYP3A4 under physiologic conditions is determined. Where there are not significant issues of toxicity from the substrate or metabolite(s), in vivo human trials may be utilized, as previously described.

The genotype of an individual is determined with respect to the provided CYP3A4 gene polymorphisms. The genotype is useful for determining the presence of a phenotypically evident polymorphism, and for determining the linkage of a polymorphism to phenotypic change.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of current techniques may be found in Sambrook et al. Molecular Cloning: A Laboratory Manual, CSH Press 1989, pp.14.2–14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy orothermethods. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided polymorphic sequences, e.g. oligonucleotides of at least 12 nt, frequently 20 nt, or larger, and including the sequence flanking the polymorphic position. Such an array may comprise a series of oligonucleotides, each of which can specifically hybridize to a different polymorphism. For examples of arrays, see Hacia et al. (1996) Nature Genetics 14:441–447; Lockhart et al. (1996) *Nature Biotechnol.* 14:1675–1680; and De Risi et al. (1996) *Nature Genetics* 14:457–460.

The genotype information is used to predict the response of the individual to a particular CYP3A4 substrate or modifier. Where an expression modifier, e.g. a macrolide drug, inhibits CYP3A4 expression, then drugs that are a CYP3A4 substrate will be metabolized more slowly if the modifier is co-administered. Where an expression modifier induces CYP3A4 expression, a co-administered substrate will typically be metabolized more rapidly. Similarly, changes in CYP3A4 activity will affect the metabolism of an administered drug. The pharmacokinetic effect of the interaction Will depend on the metabolite that is produced, e.g. a prodrug is metabolized to an active form, a drug is metabolized to an inactive form, an environmental compound is metabolized to a toxin, etc. Consideration is given to the route of administration, drug-drug interactions, drug dosage, etc.

The CYP3A4-A392/CYP3A4-G392 alternative forms are shown to be differentially distributed between broadly defined racial groups. The G form is more prevalent in African Americans, while the A form is more prevalent in American Caucasians and American Hispanics. The administration of CYP3A4 substrates and expression modifiers may be adjusted to reflect racial differences in metabolism.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

MATERIALS AND METHODS

DNA Samples. Blood specimens from approximately 300 individuals were collected after obtaining informed consent.

All samples were stripped of personal identifiers to maintain confidentiality. The only data associated with a given blood sample was gender and self-reported major racial group designations in the United States (Caucasian, Hispanic, African American). Genomic DNA was isolated from these samples using standard techniques. gDNA was either stored as concentrated solutions or stored dried in microtiter plates for future use.

PCR Amplifications. The primers used to amplify exons 5, 6, 7, 10, 12, and the promoter region of the CYP3A4 gene from 200 ng of human gDNA are shown in Table 1. Primers were designed based upon publically available cDNA and intron/exon boundary sequence, as well as intron sequences determined in our laboratory. 100 ng of gDNA from 2 individuals was amplified with the Perkin Elmer GeneAmp PCR kit according to manufacturer's instructions in 100 μl reactions with Taq Gold DNA polymerase, with one exception. Boehringer-Mannheim Expand High Fidelity PCR System kit was used to amplify intron 3. Magnesium concentrations for each PCR reaction was optimized empirically, and are shown in Table 1. Thermal cycling was performed in a GeneAmp PCR System 9600 PCR machine (Perkin Elmer) with an initial denaturation step at 95° C. for 10 min, followed by 35 cycles of denaturation at 95° C. for 30 sec, primer annealing at 55° C. for 45 sec, and primer extension at 72° C. for 2 min, followed by final extension at 72° C. for 5 min, with the following exceptions. Annealing temperature for the promoter fragment was 58° C. Cycling conditions for intron 3 were an initial denaturation at 95° C. for 2 min, followed by 35 cycles of denaturation at 94° C. for 30 sec, primer annealing at 55° C. for 45 sec, and primer extension at 68° C. for 6 min, followed by a final extension at 68° C. for 7 min.

DNA Sequencing. PCR products from 32 individuals, approximately ⅓ representing each of the 3 major racial groups (see above), were spin column purified using Microcon-100 columns. Cycle sequencing was performed on the GeneAmp PCR System 9600 PCR machine (Perkin Elmer) using the ABI Prism dRhodamine Terminator Cycle Sequencing Ready Reaction Kit according to the manufacturer's directions. Oligonucleotide primers used for the sequencing reactions are listed in Table 2. 8 μl sequencing reactions were subjected to 30 cycles at 96° C. for 20 sec, 50° C. for 20 sec, and 60° C. for 4 min, followed by ethanol precipitation. Samples were evaporated to dryness at 50° C. for ~15 min and resuspended in 2 μl of loading buffer (5:1 deionized formamide: 50 mM EDTA pH 8.0), heated to 65° C. for 5 min, and electrophoresed through 4% polyacrylamide/6M urea gels in an ABI 377 Nucleic Acid Analyzer according to the manufacturer's instructions for sequence determination. All sequences were determined from both the 5' and 3' (sense and antisense) direction.

Each sequencing reaction was performed with 2 individuals' DNA pooled together. The 16 electropherograms were analyzed by comparing peak heights, looking for ~25% reduction in peak size and/or presence of extra peaks as an indication of heterozygosity. Each electropherogram result that suggested the presence of a polymorphism was confirmed by individually resequencing each of the individuals' belonging to that pool on both strands.

Population Genotyping. High-throughput genotyping using TaqMan technology (ABI) was performed using standard techniques (Livak et al. (1995) *PCR Methods and Applications* 4:357–362) on the samples described above. The promoter region from 422 to −331 was amplified using oligonucleotide primers CYP3A4_Promo1A (SEQ ID NO:10) (5'-TGGCTTGTTGGGATGAATTTCAAG-3') and CYP3A4_Promo1B (SEQ ID NO:11) (5'-TTACTGGGGAGTCCAAGGGTTCTG-3') at a concentration of 1.0 mM in 25 μl reactions containing 7.5 mM MgCl$_2$. CYP3A4_APromo1, Fam-labeled (SEQ ID NO:12) (5'-TTAAATCGCCTCTCTCTTGCCCTTGTCTCTAT-3') and CYP3A4_GPromo1, Tet-labeled (SEQ ID NO:13) (5'-AATCGCCTCTCTCCTGCCCTTGTCTCTAT-3') oligonucleotide probes at a concentration of 100 nM were incorporated into the reactions for polymorphism detection. Thermal cycling was performed in a GeneAmp PCR System 9600 PCR machine (Perkin Elmer) with an initial incubation at 50° C. for 2 min, followed by an initial denaturation step at 95° C. for 10 min, followed by 45 cycles of denaturation at 95° C. for 30 sec and primer annealing/extension at 66° C. for 1 min. Results were automatically read on an LS50B (Perkin-Elmer).

RESULTS

A 664 bp fragment of the human CYP3A4 gene, which included 470 bp of the promoter region and 174 bp of exon 1, and 20 bp of intron 1 was amplified and resequenced. An adenine (A) to guanine (G) transition was identified at position −392 (from the start codon) which occurred at a frequency of approximately 30% in the racially-mixed 64 chromosomes screened by resequencing. Subsequent genotyping of 95 individuals from each of 3 broadly defined racial groups (African Americans, Hispanic Americans, and Caucasian Americans) produced the following allele frequencies:

| Group | CYP3A4-A392 | CYP3A4-G392 |
|---|---|---|
| American Caucasians | .963 | .037 |
| American Hispanics | .931 | .069 |
| African Americans | .473 | .527 |

A cytosine (C) to thymine (T) change was identified at position +52 of intron 6 which occurred at a frequency of approximately 1% in the racially-mixed 64 chromosomes screened by resequencing. A T to G change was identified at position +34 of intron 7 which occurred at a frequency of approximately 19% in the racially-mixed 64 chromosomes screened by resequencing. A silent mutation C to T was identified at position 579 of exon 7 that occurred at a frequency of approximately 3% in the racially-mixed 64 chromosomes screened by resequencing. A G to C change was identified at position −9 of intron 4 which occurred at a frequency of approximately 1.5% in the racially-mixed 64 chromosomes screened by resequencing. A G to A change was identified at position +12 of intron 10 which occurred at a frequency of approximately 14% in the racially-mixed 64 chromosomes screened by resequencing. A C to T change was identified at position −11 of intron 11 which occurred at a frequency of approximately 12% in the racially-mixed 64 chromosomes screened by resequencing. A dinucleotide microsatelite sequence, (CA)16 was identified approximately 500 bp into intron 3 in a single person. Table 3 contains a summary of all the polymorphisms identified.

A 664 bp fragment of the 5' region of CYP3A4 gene was sequenced in 64 chromosomes representative of three major ethnic groups. The 470 bp of the promoter region amplified contains the TATA, the CMT boxes and the octamer motif, as well as major regulatory elements such as the basic-transcription element, the NFSE, the p53 binding motif, the AP-3 binding site, a progesterone-glucocorticoid and two estrogen response elements, and a hepatic nuclear factor-5 response element. The polymorphism at position –392 lies in the 7th position of the 10 bp NFSE. Evidence from previous studies suggest that the NFSE is part of the regulatory region for CYP3A4 transcription (Hashimoto et al. (1993) *Eur J Biochem* 218:585–595).

The A to G change nucleotide change observed in the CYP3A4 NFSE at position 7 produces the sequence found in the CYP3A5 NFSE at position 7. Because the NFSE may partially account for differential expression of CYP3A4 and CYP3A5, this change in CYP3A4 could alter levels of expression and/or tissue specificity, perhaps making it more similar to the expression pattern of CYP3A5.

Allelic frequencies for the –392 polymorphism vary dramatically among the three populations tested. Several hypotheses may explain this phenomenon. This result may be due to genetic drift in the Caucasian and Hispanic populations that has severely restricted transmission, by chance alone, of the most frequent allele in African Americans. A shift in frequency of this magnitude seems unlikely for a locus in large human populations to experience simply by chance. Alternatively, a founder effect could account for this result, but this is also extremely unlikely for large, outbred populations collected without phenotypic selection or ascertainment bias. Another possibility is that natural selection has acted upon this locus, to perhaps restrict the G allele in modern Caucasian and Hispanic populations that originally arose from an African founder population (Cavalli-Sforza et al. The history and Geography of human genes. Princeton: Princeton University Press, 1994) in which the G allele was very common. Alternatively, the G allele may provide a selective advantage in the African environment, so that it has been maintained at a high frequency in the African American population that has only recently migrated from Africa. This hypothesis directly implies that this polymorphism affects CYP3A4 expression, and may be important in modulating metabolism of xenobiotic and pharmaceutical agents.

The (CA)n repeat in intron 3 is very useful, as polymorphisms of this type usually are highly polymorphic in human populations with many alleles represented. This polymorphism is therefore useful in genetic transmission studies and provides a genetic "handle" for larger numbers of CYP3A4 gene haplotypes. The alterations identified at positions –9 and –11 of introns 4 and 11 respectively may vary the efficiency of mRNA post transcriptional processing because of their proximity to the intron/exon boundries.

TABLE 1

PCR primers and Mg++concentrations.

| SEQ.ID.NO: | Region | | [Mg++] |
|---|---|---|---|
| 14 | Promoter | TGAGGAGTTTGGTGAGG | 2 mM |
| 15 | | CAAGAAACAGAGAAGAGG | |
| 16 | Exon 5 | CCCACACAAATACATCC | 2 mM |
| 17 | | AGAAGACATGGCTTTCC | |
| 18 | Exon 6 | TGTCACTTACTGCTCCA | 1 mM |
| 19 | | CAACAGGAAACCCACA | |
| 20 | Exon 7 | TCCACAATCAATACATGC | 2.5 mM |
| 21 | | CCTGAAGCCAGCAGA | |
| 22 | Exon 12 | CATCTCAACAAGACTGAAAG | 1.1 mM |
| 23 | | TGAACTCCAGAACTGAAG | |
| 24 | Intron 3 | GGCTTTTGTATGTTTGAC | 1 mM |
| 25 | | CGGTTTGTGAAGACAG | |
| 26 | Intron 10 | CCTTGGGGAAAACTGGAT | 1.5 mM |
| 27 | | CGGCCTGGGAAGTGGTG | |

TABLE 2

Sequencing primers.

| SEQ.ID.NO: | Region | Forward Primer |
|---|---|---|
| 28 | Promoter(1) | TGAGGAGTTTGGTGAGG |
| 29 | | CAAGAAACAGAGAAGAGG |
| 30 | Promoter(2) | GTGAGTGGTGTGTGTGTG |
| 31 | | GTGATTCAGTGAGGCTGT |
| 32 | Exon 5 | GGGATAAATCTCTATTGAGCA |
| 33 | | GCTTTCCTCAGCATGGA |
| 34 | Exon 6 | TGTCACTTACTGCTCCA |
| 35 | | CACAGGGGAGAAGATCC |
| 36 | Exon 7 | TGTCTGTCTGGACTGGAC |
| 37 | | AAAATGATGATGGTCACAC |
| 38 | Exon 12 | TAGTGTCAGGAGAGTAGAAAG |
| 39 | | GCCTAATTGATTCTTTGG |
| 40 | Exon 10 | ATTTGCCTTATTCTGGTT |
| 41 | | CTCCTGGGAAGTGGTG |
| 42 | Intron 3 | GGCTTTTGTATGTTTGAC |

TABLE 3

CYP3A4 gene polymorphisms.

| SEQ.ID NO: | Location | Polymorphisms | Position | SEQ ID NO |
|---|---|---|---|---|
| | Promoter | A to G | –392 | SEQ ID NO:3, nt 816 |
| 43 | ACAAGGGCAAGAGAGAGGC | | | |
| 44 | ACAAGGGCAGGAGAGAGGC | | | |
| | Intron 3 | CA repeat | +506 | SEQ ID NO:4, nt 560–591 |
| 45 | GGGTTTTTA | | | |
| 46 | GGGTTTTTACACACACACACACACACACACACACACACACA | | | |
| | Intron 4 | G to C | –9 | SEQ ID NO:5, nt 114 |
| 47 | TTCTGCTTTGAACTCTAGC | | | |
| 48 | TTCTGCTTTCAACTCTAGC | | | |
| | Intron 6 | T to G | +52 | SEQ ID NO:6, nt 183 |
| 49 | CCCTQCAGCTGCCTGCCAT | | | |
| 50 | CCCTCCAGCGGCCTGCCAT | | | |
| | Exon 7 | C to T | 579 | SEQ ID NO:7, nt 88 |
| 51 | AGTGAACATCGACTCTCTC | | | |
| 52 | AGTGAACATTGACTCTCTC | | | |
| | Intron 7 | T to G | +34 | SEQ ID NO:7, nt 213 |

TABLE 3-continued

CYP3A4 gene polymorphisms.

| SEQ.ID NO: | Location | Polymorphisms | Position | SEQ ID NO |
|---|---|---|---|---|
| 53 | | ATTTATCTTTCTCTCTTAA | | |
| 54 | | ATTTATCTTGCTCTCTTAA | | |
| | Intron 10 | G to A | +12 | SEQ ID NO:8, nt 293 |
| 55 | | GAGTGGATGGTACATGGAG | | |
| 56 | | GAGTGGATGATACATGGAG | | |
| | Intron 11 | C to T | -11 | SEQ ID NO:9 nt |
| 57 | | TCTACCAACGTGGAACCA | | |
| 58 | | TCTACCAATGTGGAACCA | | |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule, wherein said isolated nucleic acid molecule specifically hybridizes to and detects a CYP3A4 variant gene that differs from the CYP3A4 wild-type gene by having one or more polymorphisms selected from the group consisting of:

(a) a substitution of a G nucleotide for an A nucleotide at position −392 of the promoter of said CYP3A4 gene with respect to the start codon of said CYP3A4 gene;

(b) an insertion of nucleotides 10–51 of SEQ ID NO:46 at position +506 of intron 3 of said CYP3A4 gene with respect to the first nucleotide of said intron 3;

(c) a substitution of a C nucleotide for a G nucleotide at position −9 of intron 4 of said CYP3A4 gene with respect to the first nucleotide of exon 5;
(d) a substitution of a G nucleotide for a T nucleotide at position +52 of intron 6 of said CYP3A4 gene with respect to the first nucleotide of said intron 6;
(e) a substitution of a T nucleotide for a C nucleotide at position 579 with respect to the first nucleotide of the coding sequence of said CYP3A4 gene;
(f) a substitution of a G nucleotide for a T nucleotide at position +34 of intron 7 of said CYP3A4 gene with respect to the first nucleotide of said intron 7;
(g) a substitution of an A nucleotide for a G nucleotide at position +12 of intron 10 of said CYP3A4 gene with respect to the first nucleotide of said intron 10; and,
(h) a substitution of a T nucleotide for a C nucleotide at position −11 of intron 11 of said CYP3A4 gene with respect to the first nucleotide of exon 12;
and wherein said isolated nucleic acid molecule is selected from the group consisting of:
(i) an isolated nucleic acid molecule selected from the group consisting of: an isolated nucleic acid molecule consisting essentially of SEQ ID NO:44, an isolated nucleic acid molecule consisting essentially of SEQ ID NO:46, an isolated nucleic acid molecule consisting essentially of 18–19 contiguous nucleotides of SEQ ID NO:48, an isolated nucleic acid molecule consisting essentially of 18–19 contiguous nucleotides of SEQ ID NO:50, an isolated nucleic acid molecule consisting essentially of 15–19 contiguous nucleotides of SEQ ID NO:52, an isolated nucleic acid molecule consisting essentially of 18–19 contiguous nucleotides of SEQ ID NO:54, an isolated nucleic acid molecule consisting essentially of 18–19 contiguous nucleotides of SEQ ID NO:56, and an isolated nucleic acid molecule consisting essentially of 15–18 contiguous nucleotides of SEQ ID NO:58;
(ii) a nucleic acid probe consisting essentially of about 100 or fewer nucleotides, wherein said probe comprises said nucleic acid molecule of (i);
(iii) a recombinant nucleic acid molecule consisting essentially of said nucleic acid molecule of (i) and a vector sequence;
(iv) an isolated CYP3A4 variant gene that differs from a wild-type CYP3A4 gene only by having one or more polymorphisms selected from the group consisting of (a)–(h), wherein said isolated CYP3A4 gene comprises said nucleic acid molecule of (i);
(v) an at least 18 nucleotide fragment of the isolated CYP3A4 variant gene of (iv), wherein said fragment comprises said nucleic acid molecule of (i); and,
(vi) a nucleic acid molecule that is fully complementary to a nucleic acid molecule of (i), (ii), (iii), (iv) or (v).

2. The isolated nucleic acid molecule of claim 1, wherein said isolated nucleic acid molecule is a probe of 100 or fewer nucleotides, wherein said probe comprises said nucleic acid molecule of (i).

3. The isolated nucleic acid molecule of claim 2, wherein said probe is a probe of 50 or fewer nucleotides.

4. The isolated nucleic acid molecule of claim 2, wherein said probe is conjugated to a detectable marker.

5. An array of oligonucleotides comprising at least one probe of claim 2.

6. The isolated nucleic acid molecule of claim 1, wherein said nucleic acid molecule is the recombinant nucleic acid molecule of (iii).

7. The isolated nucleic acid molecule of claim 1, wherein said nucleic acid molecule is the isolated CYP3A4 variant gene of (iv).

8. The isolated nucleic acid molecule of claim 1, wherein said nucleic acid molecule is the at least 18 nucleotide fragment of (v).

9. The isolated nucleic acid molecule of claim 1, wherein said nucleic acid molecule is selected from the group consisting of SEQ ID NO:44, SEQ ID NO:46, SEQ ID NO:48, SEQ ID NO:50, SEQ ID NO:52, SEQ ID NO:54, SEQ ID NO:56, and SEQ ID NO:58.

10. A method of detecting a CYP3A4 gene in a nucleic acid sample, said method comprising:
(A) obtaining a nucleic acid sample that has been isolated from an individual;
(B) contacting said nucleic acid sample with a nucleic acid probe, wherein said nucleic acid probe specifically hybridizes to and detects a CYP3A4 variant gene that differs from the CYP3A4 wild-type gene by having one or more polymorphisms selected from the group consisting of:
(a) a substitution of a G nucleotide for an A nucleotide at position −392 of the promoter of said CYP3A4 gene with respect to the start codon of said CYP3A4 gene;
(b) an insertion of nucleotides 10–51 of SEQ ID NO:46 at position +506 of intron 3 of said CYP3A4 gene with respect to the first nucleotide of said intron 3;
(c) a substitution of a C nucleotide for a G nucleotide at position −9 of intron 4 of said CYP3A4 gene with respect to the first nucleotide of exon 5;
(d) a substitution of a G nucleotide for a T nucleotide at position +52 of intron 6 of said CYP3A4 gene with respect to the first nucleotide of said intron 6;
(e) a substitution of a T nucleotide for a C nucleotide at position 579 with respect to the first nucleotide of the coding sequence of said CYP3A4 gene;
(f) a substitution of a G nucleotide for a T nucleotide at position +34 of intron 7 of said CYP3A4 gene with respect to the first nucleotide of said intron 7;
(g) a substitution of an A nucleotide for a G nucleotide at position +12 of intron 10 of said CYP3A4 gene with respect to the first nucleotide of said intron 10; and,
(h) a substitution of a T nucleotide for a C nucleotide at position −11 of intron 11 of said CYP3A4 gene with respect to the first nucleotide of exon 12;
and wherein said nucleic acid probe is selected from the group consisting of:
(i) a nucleic acid probe consisting essentially of a nucleic acid sequence selected from the group consisting of SEQ ID NO:44, SEQ ID NO:46, 18–19 contiguous nucleotides of SEQ ID NO:48, 18–19 contiguous nucleotides of SEQ ID NO:50, 15–19 contiguous nucleotides of SEQ ID NO:52, 18–19 contiguous nucleotides of SEQ ID NO:54, 18–19 contiguous nucleotides of SEQ ID NO:56, and 15–18 contiguous nucleotides of SEQ ID NO:58;
(ii) a nucleic acid probe consisting essentially of an at least 18 nucleotide fragment of an isolated CYP3A4 variant gene, wherein said variant gene differs from a wild-type CYP3A4 variant gene only by having one or more polymorphisms selected from the group consisting of (a)–(h), and wherein said fragment comprises a nucleic acid sequence selected from the group consisting of SEQ ID NO:44, SEQ ID NO:46, 18–19 contiguous nucleotides of SEQ ID NO:48, 18–19 contiguous nucleotides of SEQ ID NO:50, 15–19 contiguous nucleotides of SEQ ID NO:52, 18–19 contiguous nucleotides of SEQ ID NO:54, 18–19 contiguous nucleotides of SEQ ID NO:56, and 15–18 contiguous nucleotides of SEQ ID NO:58; and, (iii) a nucleic acid probe that is fully complementary to a nucleic acid sequence of (i) or (ii); and, (C) detecting specific hybridization between said probe and said nucleic acid sample as indicative of the presence of a CYP3A4 gene in said nucleic acid sample.

11. The method of claim 10, wherein said step of contacting comprises contacting said nucleic acid sample with an array of oligonucleotides comprising said nucleic acid probe.

12. The method of claim 10, wherein said nucleic acid sample is a genomic DNA sample.

13. The method of claim 10, wherein said nucleic acid sample is an RNA sample.

14. An isolated nucleic acid molecule which specifically hybridizes to and detects CYP3A4 variant gene that differs from the CYP3A4 wild-type gene by having one or more polymorphisms, wherein said isolated nucleic acid molecule is selected from the group consisting of:

(I) a sense strand of a CYP3A4 variant gene, wherein said variant gene differs from a wild-type CYP3A4 gene in that said variant gene has a single polymorphism selected from the group consisting of:

(a) a substitution of a G nucleotide for an A nucleotide at position −392 of the promoter of said CYP3A4 gene with respect to the start codon of said CYP3A4 gene;

(b) an insertion of nucleotides 10–51 of SEQ ID NO:46 at position +506 of intron 3 of said CYP3A4 gene with respect to the first nucleotide of said intron 3;

(c) a substitution of a C nucleotide for a G nucleotide at position −9 of intron 4 of said CYP3A4 gene with respect to the first nucleotide of exon 5;

(d) a substitution of a G nucleotide for a T nucleotide at position +52 of intron 6 of said CYP3A4 gene with respect to the first nucleotide of said intron 6;

(e) a substitution of a T nucleotide for a C nucleotide at position 579 with respect to the first nucleotide of the coding sequence of said CYP3A4 gene;

(f) a substitution of a G nucleotide for a T nucleotide at position +34 of intron 7 of said CYP3A4 gene with respect to the first nucleotide of said intron 7;

(g) a substitution of an A nucleotide for a G nucleotide at position +12 of intron 10 of said CYP3A4 gene with respect to the first nucleotide of said intron 10; and, (h) a substitution of a T nucleotide for a C nucleotide at position −11 of intron 11 of said CYP3A4 gene with respect to the first nucleotide of exon 12;

(II) an at least 18 nucleotide fragment of the sense strand of (I), wherein said fragment includes the single polymorphism present in the sense strand of (I); and (III) a nucleic acid molecule fully complementary to (I) or (II).

15. The isolated nucleic acid molecule of claim 1, wherein said molecule further comprise an exogenous CYP3A4 promoter operably linked to a reporter gene.

* * * * *